United States Patent [19]  
Lau et al.

[11] Patent Number: 4,788,268  
[45] Date of Patent: Nov. 29, 1988

[54] METHOD FOR PREPARATION OF EPOXYSILICONE COMPOUNDS AND ALLYL-TERMINATED SILICONE COMPOUNDS

[75] Inventors: Kreisler S. Y. Lau, Alhambra; Susan L. Oldham, Torrance; William E. Elias, Redondo Beach, all of Calif.

[73] Assignee: Hughes Aircraft Company, Los Angeles, Calif.

[21] Appl. No.: 46,012

[22] Filed: May 5, 1987

[51] Int. Cl.$^4$ .............................................. C08G 77/04
[52] U.S. Cl. ..................................... 528/27; 549/215; 528/10; 528/32; 556/480
[58] Field of Search ................... 549/215; 528/10, 27, 528/32; 556/480

[56] References Cited

U.S. PATENT DOCUMENTS 3,516,964 6/1970 Patterson ............................. 549/215
4,082,726 4/1978 Mine et al. ........................... 549/215

Primary Examiner—Melvyn I. Marquis
Attorney, Agent, or Firm—M. E. Lachman; A. W. Karambelas

[57] ABSTRACT

Epoxysilicone compounds are prepared by first reacting a dibromobenzene compound with magnesium in anhydrous ether solvent to form a Grignard reagent and subsequently reacting the Grignard reagent with allyl bromide to form a (bromophenyl)propene compound. Next, the (bromophenyl)propene compound is converted to the corresponding Grignard reagent, which is then reacted with a compound of the formula I below

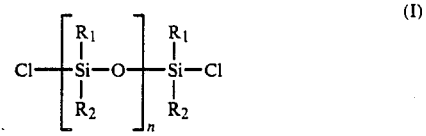

where
$n = 1$ to 6,
$R_1$ and $R_2$ are each chosen from the group consisting of a $C_1$ to $C_4$ alkyl group, a substituted aryl group, and an unsubstituted aryl group.

in tetrahydrofuran solvent to form an allyl-terminated silicone compound of formula II below

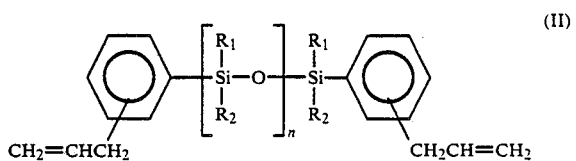

Finally, the allyl-terminated silicone compound is reacted with a chosen epoxidizing agent to form the epoxysilicone compound of formula III below.

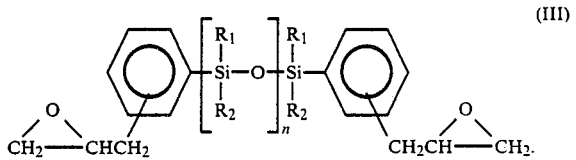

13 Claims, No Drawings

METHOD FOR PREPARATION OF EPOXYSILICONE COMPOUNDS AND ALLYL-TERMINATED SILICONE COMPOUNDS

BACKGROUND OF THE INVENTION

1. Field of the Invention

The present invention relates generally to a method for synthesizig epoxysilicone and allyl-terminated silicone compounds. More particularly, the present invention relates to a method for synthesizing epoxysilicone and allyl-terminated silicone compounds which have improved toughness, moisture stability, and thermal stability.

2. Description of the Background Art

Epoxy resins are widely used as adhesives, encapsulants, and coatings for a variety of applications. In particular, for application to structural and electronic devices and circuits, epoxy resins are useful since they provide mechanical protection, thermal and oxidation stability, good substrate adhesion, and moisture and solvent resistance. However, a problem common to the myriad of epoxy systems is the development of thermo-mechanical stresses and strains when the encapsulated devices, bonded assemblies, or coated substrates are heated or cooled. While the use of flexibilized epoxies can result in minimizing this thermal-mechanical cycling problem, such systems generally possess poor thermal stabilities. Another important property of an adhesive coating or encapsulant is its repairability. As expected, rigid systems are generally significantly more difficult to repair or replace then ductile ones.

One group of epoxy resins particularly useful for electronic applications consists of epoxysilicone compounds, which are compounds comprising silicon atoms joined together by oxygen linkages and further comprising terminal glycidyl groups. Such epoxysilicone compounds have been known for many years and are described in the publications by Bilow, Lawrence, and Patterson, "Synthesis and Polymerization of 1,3-bis-(2,3-epoxypropylphenyl)-tetramethylsiloxanes and Related Compounds," *Journal of Polymer Science*, Vol. 5, 1967, pages 2595–2615 and by Patterson and Bilow, "Polymers from Siloxane-Containing Epoxides," *Journal of Polymer Science*, Vol. 7, 1969, pages 1089–1110. As described in these references, such epoxysiloxane compounds were prepared by reacting the Grignard reagent derivable from an allylbromobenzene with a large excess of dimethyldichlorosilane. The resulting compound, chlorodimethyl(allylphenyl)silane, must be isolated from excess dichlorodimethylsilane by repeated distillation steps. Chlorodimethyl(allylphenyl)silane was then hydrolyzed to give 1,3-bis(allylphenyl)-1,1,3,3-tetramethyl-1,3-disiloxane. Epoxidation was effected either with 3-chloroperoxybenzoic acid or trifluoroperoxyacetic acid. However, such a procedure is not only tedious, but also yields a product contaminated by impurities produced by rearrangement or reversion in which —Si—O— groups break away from the rest of the molecule and form macrocycles or higher linear chains. In addition, the corrosive trifluoroperoxyacetic acid was difficult and dangerous to prepare on a large scale and the 3-chlorobenzoic acid side product generated in the epoxidation reaction was so soluble with the desired product that complete removal of this acid residue was impossible. Furthermore, such a process is not conducive to tailor making the length of the siloxane chain.

Thus, a need exists for a method of synthesizing high purity epoxysilicone compounds which form resins that exhibit toughness, repairability, thermal and oxidative stability, and moisture and solvent resistance. In addition, a need exists for a method of synthesizing the allyl compounds from which such epoxy resins, among others, may be formed.

SUMMARY OF THE INVENTION

The general purpose of the present invention is to provide a new and improved method of preparing selected epoxysilicone and allyl-terminated silicone compounds, which possesses most, if not all, of the advantages of the above-mentioned prior art methods while overcoming their above-noted significant disadvantages.

The above-described general purpose of the present invention is accomplished by first reacting a dibromobenzene compound with magnesium in anhydrous ether solvent to form a Grignard reagent and subsequently reacting the Grignard reagent with allyl bromide to form a 3-(bromophenyl)propene compound. Next, the 3-(bromophenyl)propene compound is converted, in the presence of magnesium in anhydrous tetrahydrofuran, to the corresponding Grignard reagent, which is then reacted with a compound of the formula I below

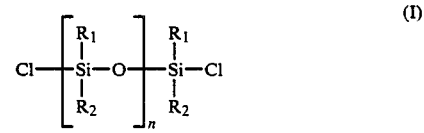

where
n = 1 to 6,
$R_1$ and $R_2$ are each chosen from the group consisting of a $C_1$ to $C_4$ alkyl group, a substitited aryl group, and an unsubstituted aryl group in tetrahydrofuran solvent to form an allyl-terminated silicone compound of formula II below.

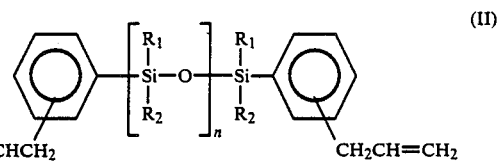

Finally, the allyl-terminated silicone compound is reacted with a chosen epoxidizing agent to form the epoxysilicone compound of formula III below.

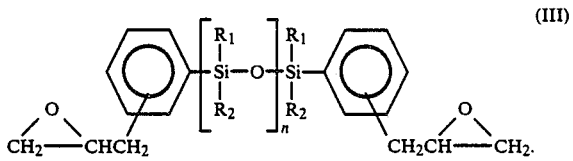

Accordingly, it is a purpose of the present invention to provide a method for synthesizing selected epoxysilicone compounds in high purity.

Another purpose of the present invention is to provide a method for synthesizing selected epoxysilicone compounds by a straightforward process which is conducive to large scale manufacture.

Yet another purpose of the present invention is to provide a method of the type described in which the internal chain length of the silicone portion of the epoxysilicone compound can be preselected.

Another purpose of the present invention is to provide a method of the type described in which an improved epoxidizing agent is used.

Still another purpose of the present invention is to provide a method for synthesizing selected allyl-terminated silicone compounds in which the internal chain length of the silicone portion of the compound can be preselected.

Another purpose of the present invention is to provide a method of the type described immediately above in which the process is straightforward and conducive to large scale manufacture.

The foregoing and other objects, features, and advantages of the present invention will be apparent from the following more particular description of the preferred embodiments of the invention.

DETAILED DESCRIPTION OF THE INVENTION

The methods of the present invention generally comprises the following steps:

(a) reacting a meta- or para-dibromobenzene compound with magnesium in anhydrous ether solvent to form a first Grignard reagent and subsequently reacting the first Grignard reagent with allyl bromide to form a 3-(bromophenyl)propene compound;

(b) reacting said 3-(bromophenyl)propene compound with magnesium in anhydrous tetrahydrofuran to form a second Grignard reagent and subsequently reacting the second Grignard reagent with a compound of the formula I below

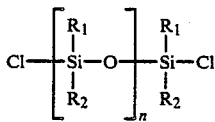

where
n=1 to 6,
$R_1$ and $R_2$ are each chosen from the group consisting of a $C_1$ to $C_4$ alkyl group, a substituted aryl group, and an unsubstituted aryl group,
in anhydrous tetrahydrofuran solvent to form the allyl-terminated silicone compound of formula II below

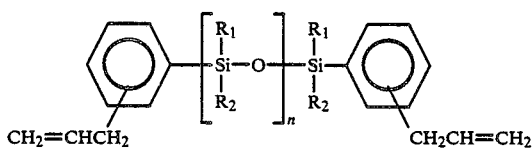

(c) reacting the compound of formula II with a chosen epoxidizing agent to form the epoxysilicone compound of formula III below

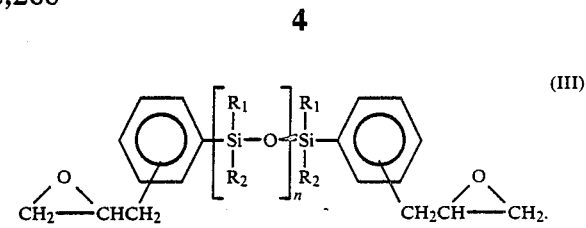

With regard to step "a" above, if meta-dibromobenzene is used, the product of step "a" is 3-(3-bromophenyl)propene, which will ultimately result in products of formulas II and III above in which the allyl or glycidyl group is attached to the benzene ring at the position meta to the silicon attachment to the benzene ring. If para-dibromobenzene is used, the product of step "a" is 3-(4-bromophenyl)propene, which will ultimately result in products of formulas II and III in which the allyl or glydicyl group is attached to the benzene ring at the position para to the silicon attachment. The synthesis method of step "a" uses the Grignard reaction, which is generally known and described, for example, by L. F. Fieser and M. Fieser, "Reagents for Organic Synthesis," Vol. 1, John Wiley and Sons, Inc., New York, 1967, pages 415–424.

With regard to step "b" above, by appropriate choice of the dichlorosiloxane reactant of formula I above, the internal chain length of the silicone portion of the products of formulas II and III can be predetermined and selected to enhance particular properties. For example, increasing the chain length from n=1 to n=3 in formula I lowers the glass transition temperature of the resulting para isomer (of formula III) after cure from 6°–24° C. to −17° C. when 1,3-bis(3-aminopropyl)1,1,3,3-tetramethyl-1,3-disiloxane was used as a curing agent. In formula I, the groups $R_1$ and $R_2$ may each be an alkyl group containing 1 to 4 carbon atoms or an aryl group, such as phenyl, naphthyl, anthryl, or phenanthryl, which may optionally be substituted with, for example, a methyl, carboxyl, or halogen group, in the meta or para position with respect to the silicon attachment.

With regard to the epoxidation process of step "c" above, it is known that 3-chloroperoxybenzoic acid (MCPBA) has been commercially used as an epoxidizing agent, and is described by Fieser and Fieser in the book entitled "Reagents for Organic Synthesis," Wiley-Interscience, New York, 1967, Vol. 1, at page 135. However, when MCPBA was used to effect epoxidation of compounds of formula II where n=1 to 3, it was found that the final product of formula III formed therefrom produced erratic results when subsequently cured. The cause of these erratic results was determined to be the residual 3-chlorobenzoic acid and its derivatives which were side products of the epoxidation process. Some of the erratic cure behavior was eliminated by treating the compound with sodium bicarbonate/sodium hydroxide solutions prior to cure and then using a high temperature cure. However, due to the problem caused by the residual 3-chlorobenzoic acid derivatives, a better epoxidation agent was sought and is described below.

In step "c" above, we have discovered that when epoxidizing a compound of formula II where n=1 to 3, a superior yield is obtained by using, as the epoxidizing agent, trichloroperoxyimidic acid (TCPIA) generated in situ by the reaction of trichloroacetonitrile and 30 percent hydrogen peroxide in a biphasic medium, such as water and dichloromethane. (The use of TCPIA to epoxidize 1-nonene was disclosed by Arias et al in the publication entitled "Epoxidation of Alkenes with Trichloroacetonitrile/Hydrogen Peroxide in a Neutral Biphasic Solvent System," in the *Journal of Organic Chemistry*, Vol. 48, 1983, pages 888–890.) In practicing the present invention, a series of compounds was epoxidized with TCPIA and it was found that unexpectedly high yields of epoxidized product were obtained when compounds of formula II were epoxidized with TCPIA. The test results indicating percentage yield of epoxidized product for a variety of substrates is presented in Example 2, item E herein. When TCPIA was used to effect epoxidation in accordance with the process of the present invention, the solid non-acidic side product of the reaction, namely trichloroacetamide, was found to be insoluble in 1:3 by volume dichloromethane-hexane and could be effectively removed. Thus, the use of TCPIA to effect epoxidation in accordance with the process of the present invention provides a high purity final product, by a straight-forward process which avoids the tedious work-up procedure required by the prior art methods. However, TCPIA was found effective for the epoxidation of a compound of formula II only where n=1 to 2. For n=3 to 6 in formula II, the TCPIA reactivity was not sufficient to cause any reaction. Consequently, in the case where n=3 to 6 in formula II, the epoxidizing agent found effective comprises 3-chloroperoxybenzoic acid (MCPBA). It has been found advantageous to use MCPBA since this compound is an inexpensive and efficient epoxidation reagent.

Typical preferred compounds formed in accordance with the process of the present invention having formula III have n, $R_1$ and $R_2$ as noted below:

| n | $R_1$ | $R_2$ |
|---|---|---|
| 1 | $CH_3$ | $CH_3$ |
| 2 | $CH_3$ | $CH_3$ |
| 3 | $CH_3$ | $CH_3$ |
| 1 | $CH_3$ | $C_6H_5$ |
| 1 | $C_6H_5$ | $C_6H_5$ |

Typical preferred compounds formed in accordance with the process of the present invention having formula II, have n, $R_1$ and $R_2$ as noted above.

The epoxysilicone compounds formed in accordance with the present process may be polymerized, using known epoxy curing agents, such as 1,3-bis(3-aminopropyl)-1,1,3,3-tetramethyl-1,3-disiloxane, 1,3-bis(3-aminobutyl)-1,1,3,3-tetramethyl-1,3-disiloxane, triethylenetetraamine, meta-phenylenediamine, 4,4'-methylene dianiline, diaminodiphenylsulfone, nadic methyl anhydride, methyl hexahydrophthalic anhydride, 2-ethyl-4-methyl-imidazole, or other amine, amide, acid, and miscellaneous nitrogen-containing curing agents to form resin. The polymers so formed exhibit improved toughness, thermal and oxidative stability, moisture-resistance, solvent-resistance, and repairability. Example 3 presents a detailed discussion of such resins and their improved performance characteristics.

In addition, the epoxysilicone compounds formed in accordance with the present process may be used as a modifier for epoxy resins in order to improve the flexibility of these resins. The epoxysilicone compound is mixed with the epoxy resin and the mixture is cured to form a copolymer, using a known epoxy curing agent, such as DGEBA (the diglycidyl ether of Bisphenol A), of which EPON 825 (obtained from Shell Chemical) is an industry standard, epoxy phenol novalacs (such as DEN 431, obtained from Dow Chemical), or digylicidylanilines (such as Glyamine 125, obtained from FIC.). The epoxy-silicone compound of the present invention comprises 10 to 80 percent by weight of the mixture, most preferably 20 to 50 percent by weight. Such modified epoxy resin formulations are discussed in greater detail in Example 9.

The allyl-terminated silicone compounds formed in accordance with the present process may be epoxidized as noted above to form epoxysilicone compounds. In addition, the allyl-terminated silicone compounds of the present invention may be polymerized using known olefin polymerization techniques such as described in S.R. Sandler and W. Karo, in "Polymer Syntheses", Volume III, Chapter 8, Academic Press, 1980. Such polymers exhibit improved toughness, thermal and oxidative stability, moisture- and solvent-resistance, and repairability. In addition, these allyl-terminated silicone compounds may be copolymerized with other materials, such as N-(vinylphenyl)phthalimide, using known methods such as described by Sandler and Karo, referenced above. The rigidity of these copolymers can be tailored by proper selection of the percent of allyl-terminated silicone compound used to form the copolymer.

Examples of practice of the process of the present invention are as follows.

EXAMPLE 1

This example illustrates the preparation of 1,3-bis(4-allylphenyl)-1,1,3,3-tetramethyl-1,3-disiloxane (Compound 3) and 1,3-bis(4-glycidylphenyl)-1,1,3,3-tetramethyl-1,3-disiloxane (Compound 4) in accordance with the processes of the present invention.

A. Preparation of 3-(4-bromophenyl)propene.

In accordance with accepted laboratory practice, the glassware used for the Grignard reaction described below was flame-dried and the interior purged with dry nitrogen. A small portion of 695 g (2.94 moles) 1,4-dibromobenzene crystals was added to 82.842 g (3.41 g-atoms) of magnesium turnings in 1500 ml of anhydrous ether. Initiation of the reaction was generally difficult. A small scale reaction was therefore started in a test tube and then added to the contents of the large reaction vessel. This was done twice. The reaction started upon further stirring. Small portions of 1,4-dibromobenzene were periodically added to the flask to maintain a slow reflux. As the dibromobenzene crystals were added to the reaction mixture, the vigor of the reaction subsided for a few seconds, and then immediately resumed. After addition was completed, the mixture was heated at reflux for 1.5 hours after addition was completed. A solution of 382.6 g (3.16 moles) of allyl bromide in 150 ml of anhydrous ether was added dropwise to the flask. Upon complete addition, the flask was stirred 0.5 hr at room temperature, then heated at a gentle reflux for 1 hour.

The mixture was poured into 2 liters of water and left to stand overnight. The layers were separated. The water layer was acidified to a pH of 2.5 and washed three times with ether.

All the ethereal solutions were combined and dried over magnesium sulfate for 1 hour. The dried solution was filtered and concentrated. The concentrate was distilled (bp 94° C./3–4 torr) to yield 295 g (1.50 moles)

of material (yield, 50.9%). The pot residue solidified on cooling. There was also a fair amount of material that was distilled over before the desired product was distilled. The product had a strong but pleasant spicy aroma. Characterization of the product was by means of infrared (IR) and nuclear magnetic resonance (NMR) spectrometries: IR (film). 2960 (strong), 1625 (weak), 1400 (medium), 1260 (strong, sharp), 1050 (strong, broad), and 800 cm$^{-1}$ (strong, broad).

NMR (CDCl$_3$): δ3.30 (bd, 2H, benzylic H's) 4.92, 5.15 (2 bm, 2H, geminal vinyl H's), 5.56–6.31 (m, 1H, vinyl H) and 7.20 ppm (q, 4H, J=8 Hz, aromatic).

B. Preparation of 1,3-bis(4-allylphenyl)-1,1,3,3-tetramethyl-1,3-disiloxane.

The compound 1,3-bis(4-allylphenyl)-1,1,3,3-tetramethyl-1,3-disiloxane [Compound (3) below], was prepared in accordance with the following reaction:

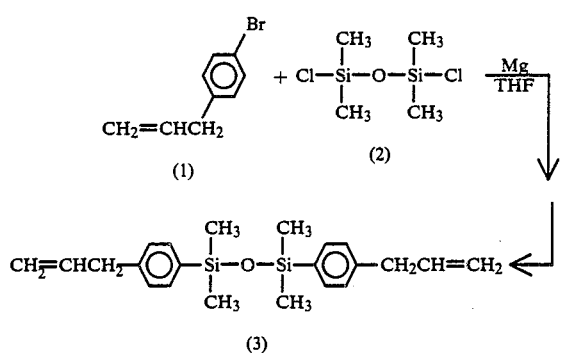

A 295-g (1.50 moles) quantity of 3-(4-bromophenyl)-propene, Compound (1) above, prepared as described in "A" above, was mixed with 200 ml of anhydrous tetrahydrofuran (out of a fresh bottle or preferably distilled from sodium) and added dropwise to a flask containing 40 g (1.64 g-atoms) of magnesium and 500 ml of anhydrous tetrahydrofuran. Tne reaction started after a short induction period. After complete addition of Compound (1), the mixture was heated at reflux for 1 hour. Exactly 150 g (0.739 moles) of 1,3-dichloro-1,1,3,3-tetrametnyl-1,3-disiloxane, Compound (2), was dissolved in 200 ml of anhydrous tetrahydrofuran and added dropwise. Upon complete addition, the mixture was gray-black. It was heated at reflux for 1.25 hours.

The mixture was poured into 200 ml of saturated ammonium chloride, and separated. The water layer was washed four times with ether. The combined organic solutions were dried over magnesium sulfate and filtered. The concentrated filtrate was subjected to 0.1 torr at 25° C. for 18 hours. The yield was 266 g (0.727 moles), 98.3%. The NMR spectrum of the product agrees with the chemical structure indicated above for Compound (3). NMR (CDCl$_3$): δ0.30 (s, 12H, SiCH$_3$), 3.34 (bd, 4H, benzylic H's), 4.90, 5.18 (2 bm, 4H, geminal vinyl H's), 5.62 –6.31 (bm, 2H, vinyl H's), and 7.32 ppm (q, 8H, J=4 Hz, aromatic).

Product batches that appeared to be dark yellow or brown could be diluted with dichloromethane, treated with activated charcoal and filtered through Celite (a diatomaceous earth). Tne concentrated filtrate would then have a light yellow color.

C. Preparation of 1,3-bis(4-glycidylphenyl)- 1,1,3,3-tetramethyl-1,3-disiloxane.

The compound 1,3-bis(4-glycidyphenyl)-1,1,3,3- tetramethyl-1,3-disiloxane, Compound (4) below, was prepared in accordance with the following reaction:

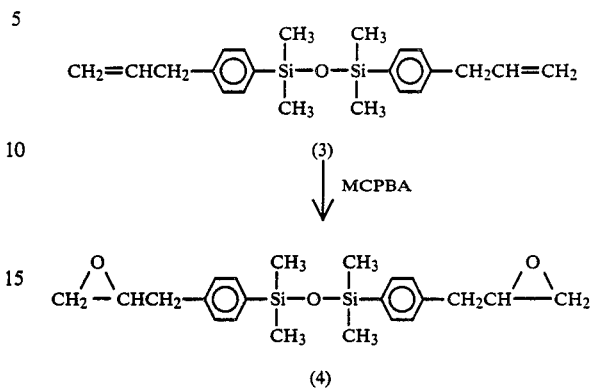

A 3-liter reaction flask was set up with a condenser and a stirrer. A 244.6-g (0.668 moles) guantity of 1,3-bis(4-allylphenyl)-1,1,3,3-tetramethyl-1,3-disiloxane, Compound (3), prepared as described in "B" above, and 1.3 liters of dichloromethane were placed into the flask. The solution was cooled with an ice bath, and treated with 278.4 g of commercial 3-chloroperoxybenzoic acid (MCPBA) (80% assay, 222.7 moles, 1.05 molar equivalent). The MCPBA was slowly added in portions, since the reaction was exothermic. After all the MCPBA was added and the exotherm had subsided, the ice bath was removed and the reaction warmed to room temperature. The mixture was then heated to reflux for three hours and cooled. The precipitated 3-chlorobenzoic acid was removed by filtration and the filtrate was allowed to stand at 0° C. for 18 hours.

More 3-chlorobenzoic acid precipitated, and was removed by a second filtration. After solvent removal, the residual yellow oil was dissolved in ether and washed three times with saturated aqueous sodium bicarbonate, twice with saturated aqueous ammonium chloride, and twice with water. The solution was dried over magnesium sulfate and the ether evaporated. The residual yellow oil was pumped at 0.1 torr/25° C. for 24 hr. NMR indicated complete absence of allylic absorptions and showed a typical absorption pattern for an epoxide compound. NMR(CDCl$_3$): δ0.31(s, 12H, SiCH$_3$), 2.42–3.31 (3 bm, 10H, characteristic of glycidyl groups) and 7.20–7.70 ppm (distorted q, 8H, aromatic). The epoxy equivalent weight of the product was 219 (theoretical:199).

EXAMPLE 2

This example illustrates the preparation of 1,3-bis(3-allylphenyl)-1,1,3,3-tetramethyl-1,3-disiloxane (Compound 5) and 1,3-bis(3-glycidylphenyl)-1,1,3,3-tetramethyl-1,3-disiloxane, Compound (6), in accordance with the processes of the present invention.

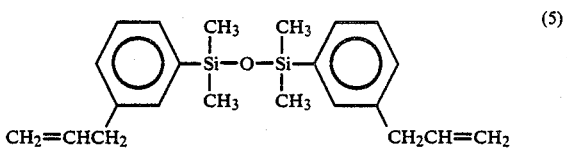

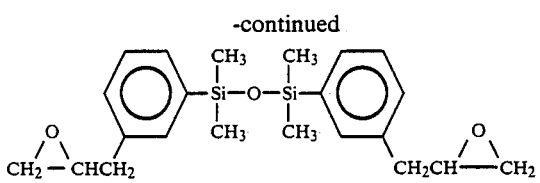

(6)

A. Preparation of 3-(3-bromophenyl)propene.

In accordance with accepted laboratory practice, the glassware used for the Grignard reaction described below was flame dried and purged with dry nitrogen. A small portion of a solution of 118 g (0.50 moles) of 1,3-dibromobenzene in 50 ml of anhydrous ether was added to 14.132 g (0.581 g-atoms) of magnesium turnings in 150 ml of anhydrous either. The reaction was initiated almost immediately to form the Grignard reagent. (In situations where reaction does not proceed immediately, a few drops of ethyl iodide may be added to induce a reaction.) After a steady reflux was established, the rest of the dibromobenzene solution was added dropwise to maintain the reflux. The total addition required 45 minutes. The final mixture was heated for an additional hour. A solution of 46 ml of allyl bromide (65 g, 0.537 moles) in 50 ml of anhydrous ether was added dropwise. The final mixture was heated for an additional hour.

The mixture was poured into 1 liter of 10% sulfuric acid, and the organic phase was separated. The aqueous phase was extracted twice with 100 ml of ether. All the etheral portions were combined, washed with 100 ml of water and dried over magnesium sulfate. The concentrated filtrate was finally distilled (60°-62° C./0.5 torr or 48°-50° C./0.1 torr) to yield 81.84 g (0.416 moles, 83.2%) of a clear liquid. NMR spectrometry unequivocally established the identity of this product as the expected 3-(3-bromophenyl)propene. The NMR spectrum was similar to that of 3-(4-bromophenyl)propene described in Example 1, step "A", except the aromatic quartet was replaced by two clusters of complex multiplets, characteristic of meta ring substitution.

NMR(CDCl$_3$): δ3.16,3.28 (bd, 2H, benzylic H's), 4.82–5.22 (2m, 2H, terminal H's on olefin), 5.55–6.60(bm, 1H, olefinic H), and 6.92–7.60 ppm(2m,4H, aromatic).

B. Preparation of 1,3-bis(3-allylphenyl)-1,1,3,3-tetramethyl-1,3-disiloxane.

The compound 1,3-bis(3-allylphenyl)-1,1,3,3-tetramethyl-1,3-disiloxane (Compound 5) was prepared in accordance with the general reaction recited in Example 1, step "B", except that the bromophenyl reactant used was 3-(3-bromophenyl)propene.

A small portion of a solution of 78.18 g (0.397 moles) of 3-(3-bromophenyl)propene, prepared as described in step "A" above, in 50 ml of anhydrous tetrahydrofuran (THF) was run into a reaction flask containing 10.78 g (0.443 g-atoms) of magnesium turnings in 150 ml of anhydrous THF. The reaction was initiated in a few minutes. The rest ot the bromophenyl compound was added dropwise to maintain a steady reflux. After complete addition, the mixture was heated at reflux for 1 hour and then treated with a solution of 38.34 g (0.189 moles) of 1,3-dichloro-1,1,3,3-tetramethyl-1,3disiloxane in 50 ml of anhydrous THF. After complete addition, the mixture was heated at reflux for 1 hour.

The mixture was then cooled, poured into 1000 ml of saturated agueous ammonium chloride solution, and extracted three times with 200 ml of ether. The organic phase was separated, dried over magnesium sulfate, filtered, and concentrated to a light yellow viscous oil. After a 24-hour solvent removal under 0.1 torr, the viscous oil achieved a constant weight. The total yield was 71.4 g (0.195 moles, 98.3%). NMR spectrometry established the identity of the product material as 1,3-bis-(3-allylphenyl)-1,1,3,3-tetramethyl-1,3-disiloxane, Compound (5). The spectrum of this product showed absorptions similar to the para, paraisomer described in Example 1, step "B", except that the aromatic region was a complex multiplet.

C. Preparation of 1,3-bis(3-glycidylphenyl)-1,1,3,3-tetramethyl-1,3-disiloxane by epoxidation with 3-chloroperoxybenzoic acid.

The compound 1,3-bis(3-glycidylphenyl)-1,1,3,3-tetramethyl-1,3-disiloxane, Compound (6), was prepared as follows. A solution of 150.3 g (0.411 moles) of 1,3-bis-(3-allyphenyl)-1,1,3,3-tetramethyl-1,3-disiloxane, prepared as described in step "B" above, in 200 ml of dichloromethane was added dropwise to a solution of 186 g of 3-chloroperoxybenzoic acid (MCPBA) (80% pure, 148.8 g assay, 0.8623 mole, 1.05 molar equivalent) in 1 liter of dichloromethane at 0° C. As the slurry was warmed to 25° C., a vigorous reaction took place that required external cooling. After the exothermic surge, a copious precipitate was obtained. The mixture was heated at reflux for 3 hr, cooled, filtered and concentrated to a 300 ml volme. Refrigerantion at 0° C. overnight yielded more solids. After filtration, the dichloromethane was removed and the oil was taken up in 250 ml of ether, and extracted with 250 ml of saturated sodium bicarbonate, two washings of 100 ml of saturated ammonium chloride, and finally two washings of 100 ml of water. After drying over magnesium sulfate, the ethereal solution was concentrated and the residual yellow oil was kept under 0.1 torr pressure for 24 hours. The yield was 137.6 g (0.346 mole, 84.1%). The IR and NMR spectrometric characteristics agreed with the chemical structure of the expected product. The NMR spectrum of this product showed absorptions similar to that of Compound (4) described in Example 1, Step "C", except that the aromatic region was a complex multiplet. The epoxy equivalent measured was 224, as compared to the theoretical value of 199. The procedure described above was repeated for the synthesis of another 200-g batch of the product noted above. The epoxy equivalent measured on this second batch was 216.

It is should be mentioned that the above-noted washing with saturated sodium bicarbonate did not seem to completely remove the solid side product, 3-chlorobenzoic acid.

The procedure described above was repeated using different proportions of reactants and the data from these experiments are summarized in Table I below.

TABLE I

| | | | MCPBA EPOXIDATION | | | | | |
|---|---|---|---|---|---|---|---|---|
| | Bisallyl Compound[a] | | MCPBA[b] | | | Yield of Epoxy | | |
| Run No. | wt. (g) | mole | wt. (g) | mole | molar equiv. | wt. (g) | yield | Epoxy Equiv.[c] |
| 1 | 245 | 0.669 | 278 | 1.288 | 1.04 | 200 | 75.1% | 216 |

TABLE I-continued

| | Bisallyl Compound[a] | | MCPBA EPOXIDATION MCPBA[b] | | | Yield of Epoxy | | |
|---|---|---|---|---|---|---|---|---|
| Run No. | wt. (g) | mole | wt. (g) | mole | molar equiv. | wt. (g) | yield | Epoxy Equiv.[c] |
| 2 | 150.3 | 0.411 | 186 | 0.862 | 1.05 | 137.6 | 84.2% | 224 |
| 3 | 54.3 | 0.148 | 80 | 0.371 | 1.25 | 39.2 | 66.5% | 252 |

[a]Run Nos. 1 and 2 were carried out with 1,3-bis(3-allylphenyl)-1,1,3,3-tetramethyl-1,3-disiloxane, molecular weight = 366. Run No. 3 was carried out with 1,3-bis(4-allylphenyl)-1,1,3,3-tetramethyl-1,3-disiloxane
[b]3-chloroperoxybenzoic acid, 80% pure
[c]theoretical epoxy equivalent is 199

D. Preparation of 1,3-bis(3-glycidylphenyl)-1,1,3,3,-tetramethyldisiloxane by epoxidation with trichloroperoxyimidic acid (TCPIA).

In an alternate method, Compound (6) was prepared as follows. To a 5-liter flask there was added 1191 ml of 30% aqueous hydrogen peroxide (10.464 moles, 10 molar equivalents). Next 358.3 g (1.5697 moles, 3 molar equivalents) of potassium hydrogen phosphate was slowly added to the stirred hydrogen peroxide solution. After the phosphate was dissolved, 191.5 g (0.5232 moles, 1 molar equivalent) of 1,3-bis(3-allylphenyl)-1,1,3,3-tetramethyl-1,3-disiloxane, (Compound 5), prepared as described in step "B" above, was combined with 226.7 g (1.5697 moles, 3 molar equivalents) of trichloroacetonitrile and dissolved in 30 ml of dichloromethane.

The trichloroacetonitrile solution containing the bisallyl compound was added dropwise to the reaction flask. There was an induction period prior to an exothermic temperature surge. The rate of addition was controlled to maintain a steady reflux. The solution in the flask bubbled and foamed, due to oxygen evolution. The total addition time was 4.5 hr. The reaction was left to stir for another 0.75 hr. The flask was heated at reflux for 16 hours and then left to stand at 25° C. for 2 days. The layers were separated, and the water layer was washed three times with ether. The organic solutions were concentrated and left to stand at 0° C. for 18 hr. The oil was dissolved into ether and washed three times with saturated sodium bicarbonate solution and twice with water, and then concentrated to a yellow oil. The NMR spectrum of the product was superimposable with that obtained for the product of step "C" of this example, showing the characteristic multiplets at 2-3 ppm for the epoxide ring protons. In addition, the NMR spectrum also indicated complete absence of the allylic absorption pattern of the starting material.

The procedure described above was repeated using different molar ratios of reactants and the data from these experiments is summarized in Table II below.

It was noted that in some subsequent large scale runs (200 g to 500 g batches), epoxidation was found to be incomplete. Recycling the recovered product mixture using a fresh hydrogen peroxide solution was needed to achieve complete epoxidation. The reaction was judged to be complete when the NMR spectrum of the product showed no absorptions due to the bisallyl starting material.

E. Epoxidation studies with trichloroperoxyimidic acid.

A series of compounds was epoxidized with trichloroperoxyimidic acid and the test results are presented in Table III below. As can be seen from Table III, unexpectedly high yields of epoxidized product were obtained when compounds of formula II were epoxidized with TCPIA in accordance with the process of the present invention, as compared to TCPIA epoxidation of other compounds.

TABLE III

EPOXIDATION STUDIES WITH TCPIA

| | TCPIA Equivalent Ratio | | Reaction | Epoxidized Product Isolated |
|---|---|---|---|---|
| Substrate | CCl$_3$N | H$_2$O$_2$ | Time, hr | Yield |
| 1-nonene | 5 | 5 | 24 | 67% |
| cyclohexene | 2.5 | 2.5 | 3-6 | 60% |
| styrene | 2 | 2 | 16 | 77.8% styrene oxide 22.2% styrene |
| styrene | 2 | 6 | 18 | 100% converted |
| p-bromoallybenzene | 2 | 3 | 66 | 45% epoxide 55% unreacted alkene |
| Compound 3* | 2 | 6 | 66 | 100% converted 83.4% yield |
| Compound 3* | 2 | 6 | 18 | 100% converted 99.0% yield |
| Compound 3* (large scale) | 2 | 4 | 4 (40° C.) | 100% converted |

*Compound 3 is 1,3-bis(4-allylphenyl)1,1,3,3-tetramethyl-1,3-disiloxane

EXAMPLE 3

TABLE II

| | A Bisallyl Compound[a] | | B CCl$_3$CN[b] | | C K$_2$HPO$_4$, 3 H$_2$O[c] | | D 30% H$_2$O$_2$ solution[d] | | molar equivalent | | | | epoxy |
|---|---|---|---|---|---|---|---|---|---|---|---|---|---|
| Run No. | wt. (g) | mole | wt. (g) | mole | wt. (g) | mole | vol (ml) | mole | A | B | C | D | equiv. |
| 1 | 132.6 | 0.362 | 216 | 1.50 | 76[e] | 0.535 | 500 | 4.4 | 1 | 2.07 | 2.94 | 6.08 | 258 |
| 2 | 121.3 | 0.331 | 224 | 1.55 | 230 | 1.01 | 500 | 4.4 | 1 | 2.34 | 3.05 | 6.65 | 258 |
| 3 | 191.5 | 0.523 | 226.7 | 1.57 | 358 | 1.57 | 1,190 | 10.5 | 1 | 3 | 3 | 10 | 265 |

[a]Run Nos. 1 and 2 were carried out with 1,3-bis(4-allylphenyl)-1,1,3,3-tetramethyl-1,3-disiloxane, molecular weight = 366. Run No. 3 was carried out with 1,3-bis(3-allylphenyl)-1,1,3,3-tetramethyl-1,3-disiloxane.
[b]molecular weight = 144.5
[c]molecular weight = 228
[d]H$_2$O$_2$ solution assayed by KMnO$_4$ titration
[e]Na$_2$HPO$_4$ (molecular weight — 142) used This example illustrates the preparation of epoxysilicone polymers by curing the epoxysilicone compounds prepared in accordance with the process of the present invention. These results show that the product of the process of the present invention provides a cured resin with excellent thermal resistance, compliance, and good mechanical strength.

A. Curing of 1,3-bis(3-glycidylphenyl)-1,1,3,3-tetramethyldisiloxane [Compound (6)]

The 1,3-bis(3-glycidylphenyl)-1,1,3,3-tetramethyl-1,3-disiloxane, Compound (6), prepared as described in Example 2 using MCPBA as the epoxidizing agent (batch 1) was cured with various curing agents as indicated in Table IV. The glass transition temperature (Tg), thermal decomposition temperature (Td), and coefficient of thermal expansion (CTE) of the cured resins were measured and the test results are indicated in Table IV. This data indicates that high thermal stability with low Tg has been achieved in these systems. In addition, lapshear and T-peel specimens were made from a sample cured with HV hardener (as indicated in Tahle IV, item 2). The cured material showed good lapshear strength of 1216±179 pounds per square inch (8.4 megapascals, MPa) and a high peel strength of 19.1±0.9 pounds per inch width (3.4 Kg per centimeter width). This data indicates good mechanical strength with excellent compliance.

In another series of tests, various hardeners were used for the above-noted epoxysilicone compound which was prepared as described in Example 2 using TCPIA as the epoxidizing agent (batch 2), and the cured product was measured by differential scanning calorimetry (DSC), thermal mechanical analysis (TMA), and dynamic mechanical spectrometry (DMS), as indicated in Table v. The DMS analysis was performed using a RDS 7700 manufactured by Rheometrics, Inc. The DSC and TMA testing showed broad transition in the low-temperature range, which is advantageous for stress relaxation. The DMS testing data gave rheological-mechanical information about the glass transition as well as the storage modulus. Item I of Table IV and item 2 of Table V showed good repairability. In item 3 of Table V, peroxide was added in an attempt to react any unepoxidized allyl groups.

TABLE IV
CURE STUDIES OF COMPOUND 6
(BATCH 1)

| Item | Hardener | Tg (°C.)[a] | Td (°C.)[b] | CTE (ppm/°C.)[c] Value | Temperature Range |
|---|---|---|---|---|---|
| 1 | Silicone-amine[d] | 5 to 20 | 296 | 65 | −75 to −25 |
| 2 | HV[e] | −10 to 15 | 210 | 70–71 | −25 to 75 |
| 3 | HVU[f] | 0 | 240 | 265 | 50 to 100 |
| 4 | TETA[g] | 4 to 10 | 210 | — | — |

[a]Tg—Glass transition temperature
[b]Td—Thermal decomposition temperature
[c]CTE—Coefficient of thermal expansion
[d]Silicone-amine—1,3-bis(3-aminopropyl)-1,1,3,3-tetramethyl-1,3-disiloxane
[e]HV—eutectic amine mixture, proprietary to Hughes Aircraft Company
[f]HVU—HV hardener with Shell hardener U added as an accelerator
[g]TETA—triethylenetetramine

TABLE V
CURE ANALYSIS OF COMPOUND 6
(BATCH 2)

| Item | Hardener[d] | Tg (°C.) TMA[a] | DSC[b] | DMS[c] |
|---|---|---|---|---|
| 1 | HV | −24, 35 | −25, 35–47 | 20 (−25 to +35) |
| 2 | Silicone amine | 6–24 | 6–10 | 10 (−15 to +35) |
| 3 | Silicone | — | −25 | −2 |

TABLE V-continued
CURE ANALYSIS OF COMPOUND 6
(BATCH 2)

| Item | Hardener[d] | Tg (°C.) TMA[a] | DSC[b] | DMS[c] |
|---|---|---|---|---|
| | amine/ di-t-butyl peroxide | | | (−20 to +25) |

[a]TMA—Thermal mechanical analysis
[b]DSC—Differential scanning calorimetry
[c]DMS—Dynamic mechanical spectrometry
[d]See Table IV for identity of hardeners B. Curing of 1,3-bis(4-glycidylphenyl)-1,1,3,3-tetramethyl-1,3-disiloxane [Compound (4)]

The 1,3-bis(4-glycidylphenyl)-1,1,3,3-tetramethyl-disiloxane prepared as described in Example 1 was cured with various curing agents as indicated in Table VI. The Tg, Td, and CTE of the cured resin were measured, and the test results are indicated in Table VI. This data indicates that systems with low to moderate Tg's and high Td's are easily accomplished with a variety of hardners using the process of the present invention.

TABLE VI
CURE STUDIES OF COMPOUND 4

| Item | Hardener | Tg (°C.)[a] | Td (°C.)[b] | CTE (ppm/°C.)[c] Value | Temperature Range |
|---|---|---|---|---|---|
| 1 | Silicone-amine[d] | 6 to 24 | 220 | 81 | −75 to −25 |
| 2 | HVU[e] | 50 | 280 | 78 | −50 to −25 |
| 3 | TETA[f] | 53 | 250 | — | — |
| 4 | ACDP[g] | 77 | 250 | 70 | −75 to −25 |
| 5 | PMDA/ ATC3[h] | 37 to 40 | 280 | 81 | −75 to −25 |

[a]Tg—Glass transition temperature
[b]Td—Thermal decomposition temperature
[c]CTE—Coefficient of thermal expansion
[d]Silicone-amine—1,3-bis(3-aminopropyl)-1,1,3,3-tetramethyl-1,3-disiloxane
[e]HVU—HV hardener with Shell hardener U added as an accelerator HV—eutectic amine mixture, proprietary formulation of Hughes Aircraft Company
[f]TETA—triethylenetetramine
[g]ADCP—proprietary anhydride hardener, Anhydrides & Chemicals
[h]PMDA/ATC3—pyromellitic dianhydride, accelerated with a proprietary cobalt complex from Cordova Chemicals.

EXAMPLE 4

This example illustrates the preparation of 1,5-bis(4-allylphenyl)-1,1,3,3,5,5-hexamethyl-1,3,5-trisiloxane (Compound 7) and 1,5-bis(4-glycidylpnenyl)-1,1,3,3,5,5-hexamethyl-1,3,5-trisiloxane (Compound 8) in accordance with the processes of the present invention.

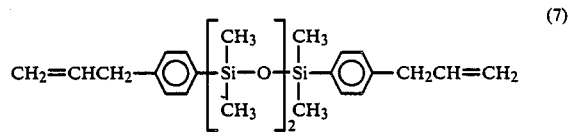

(7)

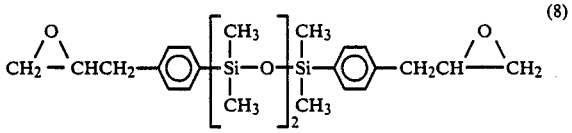

(8)

The procedure described in Example 1 was followed except that in Step "B", Compound (2) was replaced with 1,5-dichloro-1,1,3,3,5,5-hexamethyl-1,3,5-trisiloxane. The product was 1,5-bis(4-allylphenyl)-1,1,3,3,5,5-hexamethyl-1,3,5-trisiloxane (Compound 7). The latter was used as a replacement for Compound (3) in Step "C" of Example 1. The product was 1,5-bis(4-glycidylphenyl)-1,1,3,3,5,5-hexamethyl-1,3,5-trisiloxane (Compound 8). Both Compounds 7 and 8 were characterized by NMR spectrometry. The data are presented below:

Compound 7: NMR (CDCl₃) δ0.10(s, 6H, —O—Si(CH₃)₂—O—), 0.33(s,12H,O—Si(CH₃)₂—Ph), 3.43(2bs,4H,benzylic H's), 4.92,5.22(2bm,4H, geminal H's on olefin), 5.72-6.73(bm,2H,vinylH's), and 7.33 ppm (q,8H, aromatic).

Compound 8: NMR (CDCl₃) δ0.10(s,6H,—O—Si(CH₃)₂—O—), 0.33 (s,12H,—O—Si(CH₃)₂—Ph), 2.50, 2.83, 3.07(3 complex m's, 10H, diagnostic epoxide ring H's), and 7.30 ppm (q, 8H, aromatic).

EXAMPLE 5

This example illustrates the preparation of 1,7-bis(4-allylphenyl)-1,1,3,3,5,5,7,7-octamethyl-1,3,5,7tetrasiloxane (Compound 9) and 1,7-bis(4-glycidylphenyl)-1,1,3,3,5,5,7,7-octamethyl-1,3,5,7-tetrasiloxane (Compound 10) in accordance with the processes of the present invention.

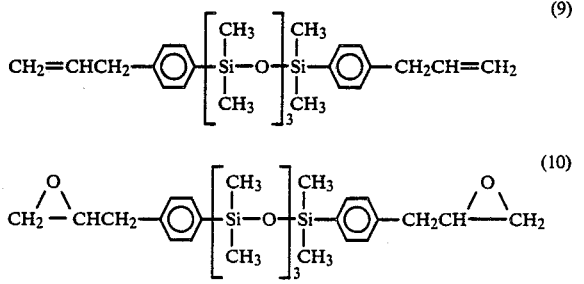

The procedure described in Example 1 was followed except that in Step "B", Compound (2) was replaced with 1,7-dichloro-1,1,3,3,5,5,7,7-octamethyl-1,3,5,7-tetrasiloxane. The product was 1,7-bis(4-allylphenyl)-1,1,3,3,5,5,7,7-octamethyl-1,3,5,7-tetrasiloxane (Compound 9). The latter was used as a replacement for Compound (3) in Step "C" of Example 1. The product was 1,7-bis(4-glycidylphenyl)-1,1,3,3,5,5,7,7-octamethyl-1,3,5,7-tetradisiloxane (Compound 10).

Both Compounds 9 and 10 were characterized by NMR spectrometry. The data are as follows:

Compound 9: NMR (CDCl₃) δ0.10(s,12H,—O—Si(CH₃)₂—O—), 0.33 (s,12H,—O—Si(CH₃)₂—Ph), 3.43(2bs,4H,benzylic H's), 4.93,5.22(2bm,4H,geminal H's on olefin), 5.68-6.60(bm,2H,vinyl H's), and 7.33 ppm(q,8H,aromatic).

Compound 10: NMR (CDCl₃) δ0.10(s,12H,—OSi(CH₃)₂—O—), 0.33(s,12H,-O-Si(CH3)2—Ph),2.50,2.83,3.07(3 complex m's, diagnostic epoxide ring H's), and 7.30 ppm(q,8H, aromatic).

EXAMPLE 6

This example illustrates the preparation of 1,5-bis(3-allylphenyl)-1,1,3,3,5,5-hexamethyl-1,3,5-trisiloxane (Compound 11) and 1,5-bis(3-glycidylphenyl)-1,1,3,3,5,5-hexamethyl-1,3,5-trisiloxane (Compound 12) in accordance with the processes of the present invention.

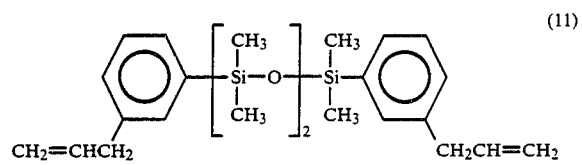

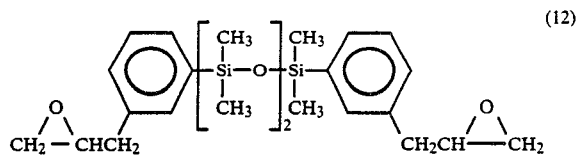

The procedure described in Example 2 was followed except that in Step "B" the dichloro compound 1,3-dichloro-1,1,3,3-tetramethyl-1,3-disiloxane was replaced with 1,5-dichloro-1,1,3,3,5,5-hexamethyl-1,3,5-trisiloxane. The product was 1,5-bis(3-allylphenyl)-1,1,3,3,5,5-hexamethyl-1,3,5-trisiloxane Compound 11). The latter was used as a replacement for 1,3-bis(3-allylphenyl)-1,1,3,3-tetramethyl-1,3-disiloxane in Step "C" of Example 2. The product was 1,5-bis(3-glycidylphenyl)-1,1,3,3,5,5-hexamethyl-1,3,5-trisiloxane (Compound 12).

The Compounds 11 and 12 were characterized by NMR spectrometry. Compounds 11 and 12 are the meta, metaisomers of Compounds 7 and 8 respectively described in Example 4. They have the corresponding NMR spectra superimposable with those of Compounds 7 and 8. The only spectral difference between Compounds 7 and 11 and between Compounds 8 and 12 is that the meta, metaisomers (i.e. Compounds 11 and 12) have a complex multiplet in the aromatic region instead of a well-defined quartet.

EXAMPLE 7

This example illustrates the preparation of 1,7-bis(3-allylphenyl)-1,1,3,3,5,5,7,7-octamethyl-1,3,5,7-tetrasiloxane (Compound 13) and 1,7-bis(3-glycidylphenyl)-1,1,3,3,5,5,7,7,-octamethyl-1,3,5,7-tetrasiloxane (Compound 14) in accordance with the processes of the present invention.

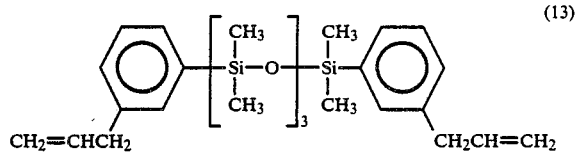

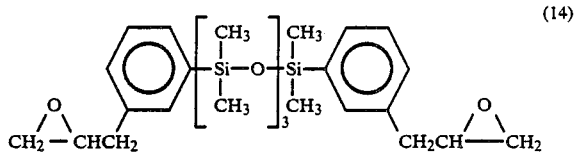

The procedure described in Example 2 was followed except that in Step "B", the dichloro compound 1,3-dichloro-1,1,3,3-tetramethyl-1,3-disiloxane was replaced with 1,7-dichloro-1,1,3,3,5,5,7,7-octamethyl-1,3,5,7-tetrasiloxane. The product was 1,7-bis(3-allylphenyl)-1,1,3,3,5,5,7,7-octamethyl-1,3,5,7-tetrasiloxane (Compound 13). The latter was used as a replacement for 1,3-bis(3-allylphenyl)-1,1,3,3-tetramethyl-1,3- disiloxane in Step "C" of Example 2. The product was 1,7-bis(3-glycidylphenyl)-1,1,3,3,5,5,7,7-octamethyl-1,3,5,7-tetrasiloxane (Compound 14).

The Compounds 13 and 14 were characterized by NMR spectrometry. Compounds 13 and 14 are the meta, metaisomers of Compounds 9 and 10 respectively described in Example 5. The NMR spectrum of Compound 13 was superimposable with that of Compound 9, except that, in the aromatic region, the quartet, characteristic of the para substitution, was replaced with a complex multiplet, characteristic of the meta substitution. Likewise is the relationship of the NMR spectral characteristics between Compounds 14 and 10.

EXAMPLE 8

This example illustrates the characterization of cured resins of 1,5-bis(4-glycidylphenyl)-1,1,3,3,5,5-hexamethyl-1,3,5-trisiloxane (Compound 8 prepared in Example 4) and 1,7-bis(4-glycidylphenyl)-1,1,3,3,5,5,7,7-octamethyl-1,3,5,7-tetrasiloxane (Compound 10, prepared in Example 5).

The resins were cured with 1,3-bis(aminopropyl)-1,1,3,3-tetramethyl-1,3-disiloxane at a 90% stoichiometry. Additional specimens were prepared with a peroxide compound (USP 245) in order to scavenge any unepoxidized allyl groups and crosslink them into the matrix. The resins of both Compounds 8 and 10 cured well, with no gummy precipitates formed when the amine curing agent was added.

The cured resins were analyzed by differential scanning calorimetry (DSC). Compound 8 had a Tg from −19° C. to −25° C. and a decomposition temperature around 280° C. This material also showed an exotherm at 209° C., probably due to the polymerization of allyl groups in the resin. The DSC scan for Compound 10 samples showed no exotherm (complete cure), a Tg between −33° C. and −31° C., and a decomposition temperature above 310° C. Both cured resins were very soft, as expected from their Tg's, and were easily repairable. The peroxide containing specimens exhibited essentially identical thermal characteristics to those without this ingredient.

EXAMPLE 9

This example illustrates the use of Compound 4 (para isomer) and Compound 6 (meta isomer), prepared as described in Examples 1 and 2 repectively, as modifiers for epoxy resins. The components in the various formulations are shown in Table VII. Each formulation was then cured as indicated in Table VIII and the thermal-mechanical data indicated in Table VIII were obtained.

TABLE VII

| MODIFIED EPOXY MATRIX FORMULATIONS | | | | | | | | |
|---|---|---|---|---|---|---|---|---|
| | Component (parts by weight) | | | | | | | |
| Formu- | Epon | DEN | Glyamine | | | | | Compound |
| lation | 825 | 431 | 125 | HV | Shell U | ACDP | 2,4EMI | 4 | 6 |
| 1 | 29.75 | 29.75 | 10.5 | 17.7 | 2.0 | — | — | 30 | — |
| 2 | 42.5 | 42.5 | 15 | 17.8 | 2.0 | — | — | — | — |
| 3 | 29.75 | 29.75 | 10.5 | — | — | 83.5 | 4 | 30 | — |
| 4 | 42.5 | 42.5 | 15 | — | — | 83.5 | 6 | — | — |
| 5 | 29.75 | 29.75 | 10.5 | 17.7 | 2.0 | — | — | — | 30 |
| 6 | 29.75 | 29.75 | 10.5 | — | — | 83.5 | 4 | — | 30 |
| 7 | 29.75 | 29.75 | 10.5 | 17.7 | 2.0 | — | — | 15 | 15 |
| 8 | 29.75 | 29.75 | 10.5 | — | — | 83.5 | 4 | 15 | 15 |

Epon 825 — a diglycidyl ether of Bisphenol A obtained from Shell Chemical.
DEN 431 — an epoxy phenol novalac obtained from Dow Chemical.
Glyamine 125 — a diglycidyl aniline obtained from FIC.
HV — eutectic amine mixture, proprietary to Hughes Aircraft Company
Shell U — an aliphatic amine obtained from Shell Chemicals.
ACDP — a proprietary anhydride obtained from Anhydrides and Chemicals.
2,4-EMI — 2-ethyl-4-methylimidazole obtained from Shikoku Chemicals, Japan.
Compound 4 is 1,3-bis(4-glycidylphenyl)-1,1,3,3-tetramethyl-1,3-disiloxane.
Compound 6 is 1,3-bis(3-glycidylphenyl)-1,1,3,3-tetramethyl-1,3-disiloxane.

TABLE VIII

| MODIFIED EPOXY MATRIX-THERMAL ANALYSIS RESULTS | | | | | |
|---|---|---|---|---|---|
| | | | DSC | | |
| | Cure Schedule | Lapshear Strength | Tg (°C.) | Tg (°C.) | |
| Formulation* | Hours At 57° C. | PSI (MPa) | Run 1 | Run 2** | Td (°C.) |
| 1 | 16 | — | 52–64 | — | >280 |
| 2 | 16 | — | 79 | 151 | 245 |
| 3 | 16 | 920 (6.3) | 78 | 136 | 280 |
| 4 | 16 | — | 78 | 136 | 288 |
| 5 | 16 | 1665 (11.5) | 74 | 85 | 300 |
| 6 | 16 | 1050 (7.2) | 75 | 114 | 255 |
| 7 | 16 | — | 72 | — | ~260 |
| 8 | 16 | — | 96 | 128 | 260 |

*Formulations are given in Table VII.
**Run 2 was performed after material was ramped past its initial exotherm to simulate post-cure.

As indicated by the data in Table VIII, in general, epoxysilicones in accordance with the present invention where n=1 depressed the Tg of the cured resins, as compared to the same resin alone. The para isomer (Compound 4) depressed the Tg only 0° to 30° C., while the meta isomer (Compound 6) depressed the Tg 30°–60° C. While peel strengths of the modified systems were low, this is easily correctable by using compounds of this invention where n=2–6 in place of n=1 as flexibilizing or toughening agents. The term "flexibilizer" is used herein to designate a material which produces a substantial depression in Tg with a significant increase in peel strength for the cured resin. The term "toughener" is used herein to designate a material which produces a minimal depression in Tg with a significant increase in peel strength of the cured resin. The meta isomers of compounds of the present invention generally act as flexibilizers; however, if a short chain length is used, they act as tougheners. The para isomers of compounds of the present invention generally act as tougheners. When used as a flexibilizer or toughening agent, the epoxysilicone compounds of the present invention are combined with other epoxy compounds in the proportion of 10 to 80 percent by weight of the present epoxysilicone in the mixture, preferably 20 to 50 percent by weight.

Thus, in accordance with the present invention as described herein, there is provided a process for forming selected epoxysilicone compounds and selected allyl-terminated silicone compounds which are cured to form tough, thermally stable, solvent resistant resins. The processes of the present invention produce these epoxysilicone and allyl-terminated silicone compounds in high purity and using straightforward processing steps. In addition, by the present process, the internal chain length of the silicone portion of the products can be predetermined and chosen to enhance selected properties. Further, in accordance with the present invention, there is provided a method for flexibilizing or toughening epoxysilicone compounds by forming copolymers thereof with the compounds formed by the present process.

Having thus described exemplary embodiments of the present invention, it should be noted by those skilled in the art that the disclosures written are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method for preparing epoxysilicone compounds comprising the steps of:
   (a) reacting a dibromobenzene compound with magnesium in anhydrous ether solvent to form a first Grignard reagent and subsequently reacting said first Grignard reagent with allyl bromide to form a 3-(bromophenyl) propene compound;
   (b) reacting said 3-(bromophenyl)propene compound with magnesium in anhydrous tetrahydrofuran to form a second Grignard reagent and subsequently reacting said second Grignard reagent with a compound of the formula I below:

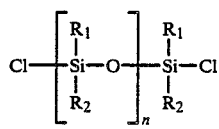

where
n = 1 to 6,
$R_1$ and $R_2$ are each chosen from the group consisting of a $C_1$ to $C_4$ alkyl group, a substituted aryl group, and an unsubstituted aryl group, in tetrahydrofuran solvent to form an intermediate compound of formula II below:

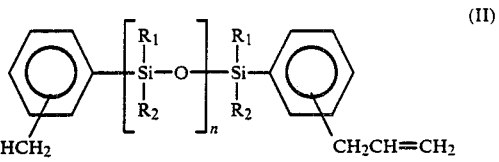

(c) reacting said compound of formula II with an epoxidizing agent selected from the group consisting of: trichloroacetonitrile and hydrogen peroxide in a biphasic medium; and 3-chloroperoxybenzoic acid, to form said epoxysilicone compound of formula III below:

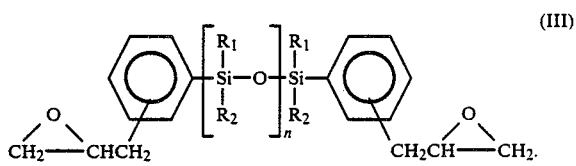

2. The method of claim 1 wherein n=1 to 2 and said epoxidizing agent comprises trichloroacetonitrile and hydrogen peroxide in a biphasic medium.

3. The method of claim 2 wherein said biphasic medium comprises water and dichloromethane.

4. The method of claim 1 wherein n=3 to 6 and said epoxidizing agent comprises 3-chloroperoxybenzoic acid.

5. The method of claim 1 wherein said dibromobenzene compound comprises 1,3-dibromobenzene and said bromophenylpropene compound formed therefrom comprises 3-(3-bromophenyl)propene.

6. The method of claim 1 wherein said dibromobenzene compound comprises 1,4-dibromobenzene and said broxophenylpropene compound formed therefrom comprises 3-(4-bromophenyl)propene.

7. A method for preparing silicone compounds having formula I below:

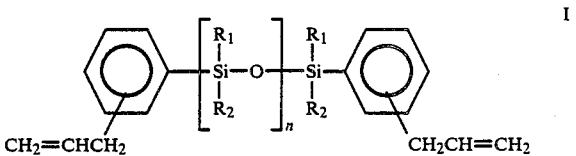

comprising the steps of:
   (a) reacting a dibromobenzene compound with magnesium in anhydrous ether solvent to form a first Grignard reagent and subsequently reacting said first Grignard reagent with allyl bromide to form a 3-(bromophenyl) propene compound;
   (b) reacting said 3-(bromophenyl)propene compound with magnesium in anhydrous tetrahydrofuran to form a second Grignard reagent and subsequently reacting said second Grignard reagent with a compound of the formula II below:

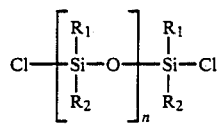

where
n=1 to 6,
R₁ and R₂ are each chosen from the group consisting of a $C_1$ to $C_4$ alkyl group, a substituted aryl group, and an unsubstituted aryl group,
in tetrahydrofuran solvent to form said compound of formula I.

8. The method of claim 7 wherein said dibromobenzene compound comprises 1,3-dibromobenzene and said bromophenylpropene compound formed therefrom comprises 3-(3-bromophenyl)propene.

9. The method of claim 7 wherein said dibromobenzene compound comprises 1,4-dibromobenzene and said bromophenylpropene compound formed therefrom comprises 3-(4-bromophenyl)propene.

10. A method for improving the flexibility of a cured epoxy resin which is formed by curing an uncured epoxy resin, comprising:
(a) forming a mixture of said uncured epoxy resin with a compound of the formula:

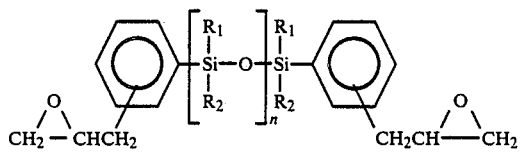

where
n=1 to 6,
R₁ and R₂ are each chosen from the group consisting of a $C_1$ to $C_4$ alkyl group, a substituted aryl group, and an unsubstituted aryl group, and
(b) curing said mixture with an epoxy curing agent to from a copolymer having improved flexibility compared to said cured epoxy resin.

11. A method according to claim 10 wherein said compound comprises about 10 to 80 percent by weight of said mixture.

12. A method for improving the toughness of a cured epoxy resin which is formed by curing an uncured epoxy resin, comprising:
(a) forming a mixture of said uncured epoxy resin with a compound of the formula:

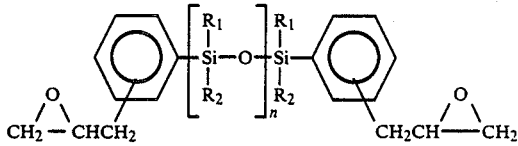

where
n=1 to 6,
R₁ and R₂ are each chosen from the group consisting of a $C_1$ to $C_4$ alkyl group, a substituted aryl group, and an unsubstituted aryl group, and
(b) curing said mixture with an epoxy curing agent to form a copolymer having improved flexibility compared to said cured epoxy resin.

13. A method according to claim 12 wherein said compound comprises about 10 to 80 percent by weight of said mixture.

* * * * *